(12) United States Patent
Schickaneder et al.

(10) Patent No.: US 10,294,208 B2
(45) Date of Patent: May 21, 2019

(54) BENDAMUSTINE DERIVATIVES AND RELATED COMPOUNDS, AND MEDICAL USE THEREOF IN CANCER THERAPY

(71) Applicant: Helmut Schickaneder, Eckental (DE)

(72) Inventors: Helmut Schickaneder, Eckental (DE); Christian Schickaneder, Lauf an der Pegnitz (DE); Armin Buschauer, Lappersdorf (DE); Stefan Huber, Regensburg (DE); Michael Limmert, Dresden (DE); Günther Bernhardt, Schierling (DE); Mathias Lubbe, Dresden (DE); Harald Hofmeier, Dresden (DE)

(73) Assignee: SYNBIAS PHARMA AG, Schaffhausen (CH)

( * ) Notice: Subject to any disclaimer, the term of this patent is extended or adjusted under 35 U.S.C. 154(b) by 0 days.

(21) Appl. No.: 15/647,257

(22) Filed: Jul. 11, 2017

(65) Prior Publication Data
US 2017/0313663 A1 Nov. 2, 2017

Related U.S. Application Data

(62) Division of application No. 14/405,996, filed as application No. PCT/EP2013/062347 on Jun. 14, 2013.

(60) Provisional application No. 61/670,158, filed on Jul. 11, 2012, provisional application No. 61/661,374, filed on Jun. 19, 2012.

(51) Int. Cl.
*A61K 31/4184* (2006.01)
*C07D 235/16* (2006.01)
*C07C 231/02* (2006.01)

(52) U.S. Cl.
CPC .......... *C07D 235/16* (2013.01); *C07C 231/02* (2013.01)

(58) Field of Classification Search
CPC .................. C07D 235/16; A61K 31/4184
USPC ....................... 548/310.1; 514/394
See application file for complete search history.

(56) References Cited

U.S. PATENT DOCUMENTS 8,809,549 B2   8/2014 Schickaneder et al.

FOREIGN PATENT DOCUMENTS

| WO | 9427954 | 12/1994 |
| WO | 2010042568 A1 | 4/2010 |
| WO | 2012059935 A9 | 6/2012 |

OTHER PUBLICATIONS

Registry database entry: CAS RN 1372789-74-6 (Entered STN: May 4, 2012). (Year: 2012).*
Teichert, J., R. Sohr, F. Baumann, L. Hennig, K. Merkle, Karel Caca, and R. Preiss, "Synthesis and Characterization of some new Phase II metabolites of the alkylator Bendamustine ( . . . ) patients with cholangiocarcinoma" Drug Metab. and Dispos. (2005), 33(7), pp. 984-992. (Year: 2005).*
Canadian Intellectual Property Office Office Action issued in Application No. 2,875,455 dated Mar. 13, 2017.
Dubbelman, et al., "Metabolite Profiling of Bendamustine in Urine of Cancer Patients after Administration of [14C] Bendamustine," Drug Metabolism and Disposition; 40(7):1297-1307, Apr. 2012.
EPO Communication issued in Application No. 13729324.7 dated Aug. 9, 2016.
International Search Report issued in application No. PCT/EP2013/062347 dated Sep. 10, 2013.
Japan Patent Office Decision to Grant a Patent issued in Application No. 2015-517698 dated May 1, 2017 (with English machine translation).
Notification to Make Divisional Application issued in counterpart Chinese application No. 201380031893 dated Dec. 8, 2015 with English translation.

(Continued)

*Primary Examiner* — Matthew P Coughlin
*Assistant Examiner* — Sagar Patel
(74) *Attorney, Agent, or Firm* — Potomac Law Group, PLLC

(57) ABSTRACT

The present invention relates to bendamustine derivatives and related compounds of formula (VII), (VIII) and (IX), and medical uses thereof in particular in cancer therapy.

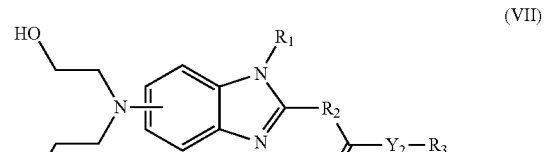

(VII)

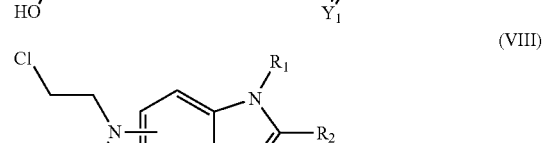

(VIII)

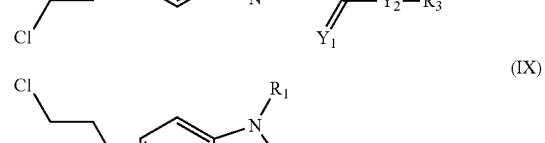

(IX)

15 Claims, No Drawings

(56) References Cited

OTHER PUBLICATIONS

Russian Agency for Industrial Property, Patents and Trademarks Office Action issued in Application No. 2014146896/04(075505) dated May 29, 2017 (with English translation).
Scutaru et al., "Bivalent bendamustine and melphalan derivatives as anticancer agents," European Journal of Medicinal Chemistry; 46(5);1604-1615, May 2011.
Scutaru, Anna Maria, et al.; "Optimization of the N-Lost Drugs Melphalan and Bendamustine: Synthesis and Cytotoxicity of a New Set of Dendrimer—Drug Conjugates as Tumor Therapeutic Agents" Bioconjugate Chem., 21 (10):1728-1743, Oct. 2010.
State Intellectual Property Office of P.R. China Office Action issued in Application No. 2017060601547920 dated Jun. 9, 2017 (wth English translation).
STN Registry database entry: CAS RN 1372789-75-7 (Entered STN: May 2, 2012).

\* cited by examiner

BENDAMUSTINE DERIVATIVES AND RELATED COMPOUNDS, AND MEDICAL USE THEREOF IN CANCER THERAPY

FIELD OF THE INVENTION

The present invention relates to bendamustine derivatives and related compounds, and medical uses thereof.

BACKGROUND OF THE INVENTION

Bendamustine (IUPAC name: 4-{5-[bis(2-chloroethyl)amino]-1-methyl-1H-benzimidazol-2-yl}butanoic acid) having the structural formula

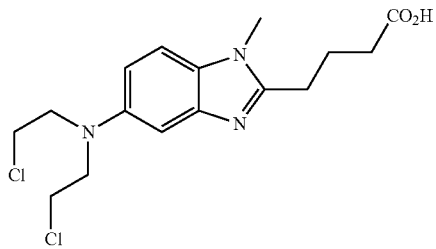 [SMILES: Cn1c(CCCC(=O)O)nc2cc(N(CCCl)CCCl)ccc21]

is a nitrogen mustard belonging to the family of drugs called alkylating agents. Bendamustine has been shown to be effective in the treatment of chronic lymphocytic leukemias and lymphomas. Bendamustine is normally used in its hydrochloride salt form as active agent. However, efficacy in terms of cytotoxicity and/or cytostaticity is a challenging issue and a critical problem.

Conventionally, bendamustine (HCl) is prepared by a process as disclosed e.g. in DD 34727 and J. Chen et al., Org. Process Res. Dev. 2011, 15, p. 1063-1072. Furthermore, DD 34727 discloses derivatives of bendamustine hydrochloride having the following structural formulae

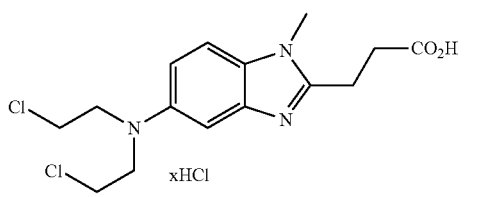

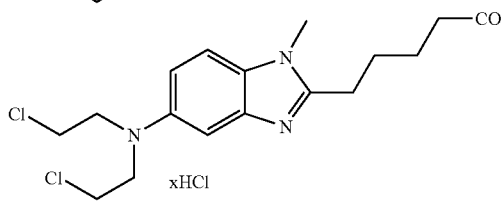

in which derivatives the carbon chain linking the carboxylic acid moiety to the benzimidazole ring structure is shortened by one methylene unit and extended by one methylene unit, respectively. However, antiproliferative activities of the aforementioned higher and the lower homologues of bendamustine have not been reported.

There is still a need for bendamustine derivatives, and thus an object of the present invention is to provide bendamustine related compounds with useful properties and therapeutical effects, and therapeutical uses thereof.

SUMMARY OF THE INVENTION

The object is solved by a compound of formula IX according to claim 1, a compound of formula VIII according to claim 4, a compound of formula VII according to claim 5, processes according to claims 10 and 17 and a pharmaceutical composition according to claim 18. Preferred embodiments are set forth below and in the subclaims.

Various aspects, advantageous features and preferred embodiments of the present invention as summarized in the following items, respectively alone or in combination, contribute to solve the object of the invention:

(1) A compound of formula IX

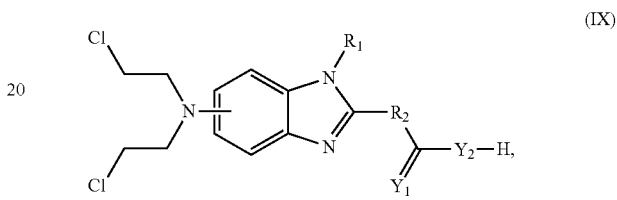

or a salt thereof, wherein $R_1$ is alkyl, aryl or alkylaryl; $R_2$ represents alkanediyl, arylene, alkylarylene or arylalkanediyl; $Y_1$ and $Y_2$ independently from each other represent oxygen or sulphur, wherein the bis(2-chloroethyl)amino-group is attached at position 4, 6 or 7 of the benzimidazole ring structure.

The terms "alkyl" and "alkanediyl" as used herein means straight, branched or cyclic hydrocarbons having a typical meaning, preferably 1 to 12 carbon atoms, preferably 1 to 8 carbon atoms and more preferably 1 to 6 carbon atoms.

The term "aryl(ene)" as used herein means hydrocarbon aryls having a typical meaning, preferably 3 to 12 carbon atoms, preferably single or condensed six-membered rings, more preferably phenyl.

The terms "alkylaryl(ene)" and "arylalkane(diyl)" as used herein mean that the aforementioned aryl(ene) moieties are incorporated into the aforementioned straight or branched alkyl or alkanediyl moieties either at one of the proximal or distal ends of the alkyl or alkanediyl chain or between the alkyl or alkanediyl chains. For example, for $R_1$, proximal end means adjacent to the nitrogen atom of the benzimidazole ring of compound of formula I, while distal means the terminal carbon of the alkyl or aryl moiety which is furthermost from said nitrogen atom. For $R_2$ proximal end means adjacent to —$CY_1$— of the —$CY_1$—$Y_2$— carboxylic acid group of compound of formula IX, while distal means the terminal carbon of the alkyl or alkanediyl moiety which is furthermost from said —$CY_1$— moiety.

The bis(2-chloroethyl)amino group is attached at position 4, 6 or 7 of the benzimidazole ring structure. The following structural formula IX'

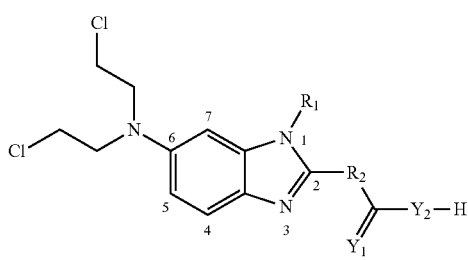

(IX')

shows an example where the bis(2-chloroethyl)amino group is in 6-position. In other examples, instead of the 6-position, the bis(2-chloroethyl)amino group is correspondingly attached either in position 4 or 7.

Preferably, the salt of compound of formula IX represents a pharmaceutically acceptable salt.

(2) The compound of formula IX according to item (1), wherein the bis(2-chloroethyl)amino group is attached to the 6 position of the benzimidazole ring structure.

(3) The compound of formula IX according to item (1) or (2), wherein $R_1$ is C1-C3 alkyl, $R_2$ represents C1-C3 alkanediyl, $Y_1$ and $Y_2$ represent oxygen.

As to the meaning of the terms "alkyl", "alkanediyl", reference is made to the explanations under item (1) above.

(4) The compound of formula IX according to any one of the preceding items, wherein $R_1$ is methyl, $R_2$ is propanediyl, and $Y_1$ and $Y_2$ represent oxygen.

The compound defined in item (4) has the structural formula

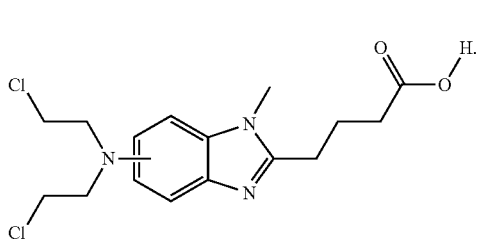

(IX")

In the following, compounds of formula IX having substituents $R_1$, $R_2$, $Y_1$ and $Y_2$ as defined in item (4) are named "iso-X-bendamustines", wherein X denotes the position of the N-lost moiety (bis(2-chloroethyl)amino group) at the benzimidazole ring structure of compound of formula IX, i.e. denotes either the 6- or the 4- or the 7-position. For example, a compound of formula IX" in which the N-lost moiety is attached to the 6-position of the benzimidazole ring structure represents "6-iso-bendamustine".

The term "conventional bendamustine" used in the following means bendamustine having the structural formula

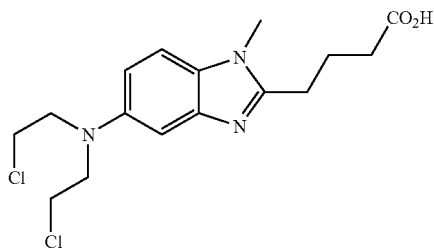 [SMILES: Cn1c(CCCC(=O)O)nc2cc(N(CCCl)CCCl)ccc21]

wherein the N-lost moiety is in 5-position of the benzimidazole ring structure.

(5) The compound according to any one of the preceding items, wherein compound of formula IX is in the form of a base addition salt in which the base is selected from the group consisting of magnesium hydroxide, calcium hydroxide, zinc hydroxide, potassium hydroxide, sodium hydroxide, potassium carbonate, sodium carbonate, potassium hydrogen carbonate, sodium hydrogen carbonate, diethylamine, triethylamine, ethanolamine (2-aminoethanol), diethanolamine (2,2'-iminobis(ethanol)), triethanolamine (2,2',2''-nitrilotris(ethanol)), ethylenediamine, piperazine, piperidine, pyrrolidine, pyridine, morpholine, 1H-imidazole, N-methyl-glucamine, L-lysine, choline, L-arginine, benethamine, 4-(2-hydroxyethyl)-morpholine, tromethamine, 2-(dimethylamino)ethanol (Deanol), 1-(2-hydroxyethyl)-pyrrolidine, 2-(diethylamino)-ethanol, benzathine, hydrabamine and betaine; or compound of formula IX is in the form of an acid addition salt according to item (18).

(6) The compound according to any one of the preceding items, wherein compound of formula IX is in the form of a salt, preferably a salt comprising 0.6 to 1.4 mol water relative to 1 mol of compound of formula IX, more preferably 0.8 to 1.2 mol water, even more preferably the salt comprising water is in the form of a hydrate.

The phrase "comprising water" as used herein means that compound of formula IX comprises the above indicated amounts of water despite of (extensive) drying (e.g. by means of drying in vacuo and/or under heating). This water may be simply adsorbed to the molecule, or it may be incorporated into the crystal lattice of it.

The term "hydrate" specifies a crystalline solid adduct wherein a stoichiometric or nonstoichiometric amount of water is incorporated in the crystal lattice of said crystalline solid. The hydrate of compound of formula IX may be free of organic solvent, but optionally may additionally have organic solvent(s) incorporated.

Preferably, a crystalline pharmaceutically acceptable salt of compound of formula IX'''

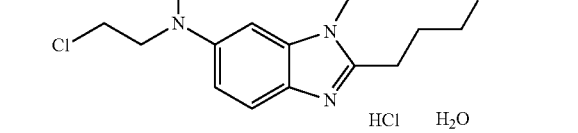

(IX''')

represents 6-iso-bendamustine hydrochloride, more preferably this compound represents a hydrate. Even more preferably, said compound of formula IX''' exhibits a X-ray diffraction (XRD) pattern having at least signals at the following 2θ values (±0.5° respectively):

| 2theta [°] | 7.83 | 10.01 | 13.18 | 13.75 | 14.96 | 15.34 | 18.47 | 22.27 | 24.63 | 26.53 |
|---|---|---|---|---|---|---|---|---|---|---|

(7) A compound of formula VIII

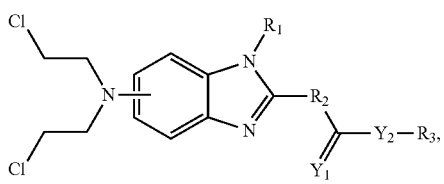

or a salt thereof,
wherein $R_1$ and $R_3$ are independently from each other selected from alkyl, aryl or alkylaryl; $R_2$ represents alkanediyl, arylene, alkylarylene or arylalkanediyl; $Y_1$ and $Y_2$ independently from each other represent oxygen or sulphur, wherein the bis(2-chloroethyl)amino group is attached at position 4, 6 or 7 of the benzimidazole ring structure; optionally, $R_3$ is substituted with an amine moiety —$NR_5R_6$ in which $R_5$ and $R_6$ independently from each other represent substituted or unsubstituted alkyl or $R_5$ and $R_6$ together represent a C3-C7 alkyl chain forming a 4- to 8-membered ring structure together with the nitrogen located between $R_5$ and $R_6$, wherein one or more carbon atoms in said ring structure is/are optionally replaced by (a) heteroatom(s) selected from the group consisting of nitrogen (N), oxygen (O) or sulphur (S).

As regards the meaning of the terms "alkyl", "alkanediyl", "aryl(ene)", "alkylaryl(ene)", and "arylalkane(diyl)", reference is made to the explanations made under item (1) above. As regards the position of the bis(2-chloroethyl)amino group at the benzimidazole ring of compound of formula (VIII), the explanations made for the bis(2-chloroethyl)amino group of compound of formula IX under item (1) apply likewise.

Preferably, the optional amine substituent —$NR_5R_6$ is located at the distal end of $R_3$ which is furthermost from $Y_2$ of the —$CY_1$—$Y_2$— moiety. The following structural formula VIII'

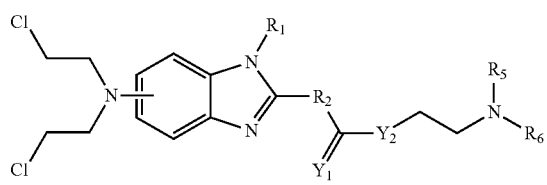

illustratively shows an example where $R_3$ represents ethylene, and the amine moiety —$NR_5R_6$ is located at the carbon of the ethylene moiety which is furthermost from $Y_2$ of the —$CY_1$—$Y_2$— moiety. In other examples, instead of ethylene, $R_3$ represents a moiety selected from the general group consisting of alkanediyl, arylene or alkylarylene or arylalkanediyl.

Preferably, the salt of compound of formula VIII represents a pharmaceutically acceptable salt.

(8) A compound of formula VII

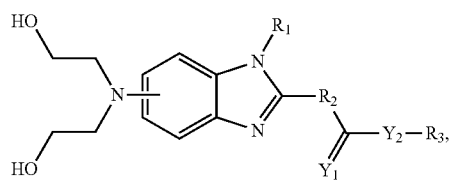

or an acid addition salt thereof,
wherein $R_1$ and $R_3$ are independently from each other selected from alkyl, aryl or alkylaryl; $R_2$ represents alkanediyl, arylene, alkylarylene or arylalkanediyl; $Y_1$ and $Y_2$ independently from each other represent oxygen or sulphur, wherein the bis(2-hydroxyethyl)amino group is attached at position 4, 6 or 7 of the benzimidazole ring structure; optionally, $R_3$ is substituted with an amine moiety —$NR_5R_6$ in which $R_5$ and $R_6$ independently from each other represent substituted or unsubstituted alkyl or $R_5$ and $R_6$ together represent a C3-C7 alkyl chain forming a 4- to 8-membered ring structure together with the nitrogen located between $R_5$ and $R_6$, wherein one or more carbon atoms in said ring structure is/are optionally replaced by (a) heteroatom(s) selected from the group consisting of nitrogen (N), oxygen (O) or sulphur (S).

As regards the meaning of the terms "alkyl", "alkanediyl", "aryl(ene)", "alkylaryl(ene)", and "arylalkane(diyl)", reference is made to the explanations made under item (1) above. As regards the position of the bis(2-hydroxyethyl)amino group at the benzimidazole ring of compound of formula (VIII), the explanations made for the bis(2-chloroethyl)amino group of compound of formula IX under item (1) likewise apply.

(9) The compound according to item (7) or (8), wherein $R_3$ is substituted with amine substituent —$NR_5R_6$ in which $R_5$ and $R_6$ independently from each other represent C1-C4 alkyl or form a 5- to 7-membered ring structure together with the nitrogen located between $R_5$ and $R_6$.

(10) The compound according to any one of items (7) to (9), wherein $R_5$ and $R_6$ are the same and represent C1-C3 alkyl or $R_4$ and $R_5$ form a 5- to 7-membered ring structure together with the nitrogen located between $R_5$ and $R_6$.

(11) The compound according to any one of items (7) to (10), wherein in the ring structure formed by $R_5$ and $R_6$ together with the nitrogen located between $R_5$ and $R_6$, one carbon atom is replaced by one nitrogen atom or one oxygen atom, preferably one oxygen atom.

(12) The compound according to item (11), wherein in the ring structure formed by $R_5$ and $R_6$, a further nitrogen atom is substituted (—$NR_7$—) or unsubstituted (—NH—), preferably substituted with $R_7$ selected from the group consisting of alkyl, aryl, alkylaryl or arylalkyl, more preferably with alkyl.

As to the meaning of the terms "alkyl", "aryl", "alkylaryl" or "arylalkyl", reference is made to the explanations under item (1) above.

(13) The compound according to any one of items (7) to (12), wherein the ring structure formed by $R_5$ and $R_6$ together with the nitrogen located between $R_5$ and $R_6$ is in the form of a 5- or 6-membered ring, preferably a 6-membered ring.

(14) The compound according to any one of items (7) to (13), wherein the ring structure formed by $R_5$ and $R_6$ together with the nitrogen located between $R_5$ and $R_6$ is selected from the group consisting of pyrrolidine, piperidine, piperazine and morpholino, preferably piperazine or morpholino, more preferably morpholino.

(15) The compound according to any one of items (7) to (14), wherein the atoms of the ring structure formed by $R_5$ and $R_6$ together with the nitrogen located between $R_5$ and $R_6$ may be unsubstituted, or substituted with a substituent selected from the group consisting of C1-C4 alkyl, C1-C4 alkoxy, C1-C4 alkylsulfide, unsubstituted amino (—$NH_2$), dialkylamino in which alkyl is C1-C4 alkyl; preferably C1-C4 alkyl or C1-C4 alkoxy; more preferably the ring structure is unsubstituted.

(16) The compound of formula VII or VIII according to any one of items (7) to (15), wherein $R_1$ is C1-C3 alkyl, $R_2$ is C1-C3 alkanediyl, $R_3$ is C1-C3 alkyl, and $Y_1$ and $Y_2$ represent oxygen.

(17) The compound of formula VII or VIII according to any one of items (7), (8) and (16), wherein $R_1$ is methyl, $R_2$ is propanediyl, $R_3$ is ethyl, $Y_1$ and $Y_2$ represent oxygen; optionally $R_3$ is substituted with —$NR_5R_6$ in which $R_5$ and $R_6$ form a morpholino moiety together with the nitrogen located between $R_5$ and $R_6$.

The compound of formula VIII defined in item (17) in which $R_3$ is substituted with —$NR_5R_6$ in the form of a morpholino moiety has the structural formula

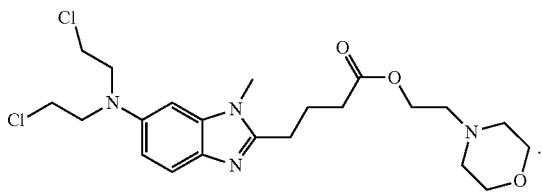 [SMILES: Cn1c(CCCC(=O)OCCN2CCOCC2)nc2ccc(N(CCCl)CCCl)cc21]

(18) The compounds of formula according to any one of the preceding items, wherein compound of formula IX, VIII or VII is in the form of an acid addition salt in which the acid is selected from the group consisting of hydrochloric acid, hydrobromic acid, sulfuric acid, phosphoric acid, glutamic acid, (+)-L-tartaric acid, citric acid, (−)-L-malic acid, DL-lactic acid, L-ascorbic acid, succinic acid, adipic acid, acetic acid, stearic acid, carbonic acid, thiocyanic acid, glycerol-phosphoric acid, L-aspartic acid, maleic acid, fumaric acid, galactaric acid, D-glucuronic acid, glycolic acid, D-glucoheptonic acid, hippuric acid, D-gluconic acid, glutaric acid, sebacic acid, capric (decanoic) acid, lauric acid, palmitic acid, alginic acid, benzoic acid, nicotinic acid, propionic acid, caprylic (octanoic) acid, naphthalene-1,5-disulfonic acid, ethane-1,2-disulfonic acid, cyclamic acid, p-toluenesulfonic acid, methanesulfonic acid, dodecylsulfuric acid, naphthalene-2-sulfonic acid, benzenesulfonic acid, oxalic acid, 2-hydroxy ethanesulfonic acid, ethanesulfonic acid, pannoic (embonic) acid, 2-oxoglutaric acid, 1-hydroxy-2-naphthoic acid, malonic acid, gentisic acid, lactobionic acid, (−)-L-pyroglutamic acid, oleic acid, (+)-camphoric acid, isobutyric acid and orotic acid.

(19) The compounds of formula IX and VIII according to any one of items (1) to (7) and (9) to (18) in the form of their free acid/base or a pharmaceutically acceptable salt thereof for use in the therapeutic treatment of diseases selected from the group consisting of acute T cell leukaemia, erythroleukemia, Ewing osteosarcoma, (hormone dependent) mamma carcinoma, cervix carcinoma, colorectal cancer, medulloblastoma, glioblastoma and astrocytoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; preferably, the disease is selected from the group consisting of acute T cell leukaemia, erythroleukemia, Ewing osteosarcoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; more preferably, the disease is selected from the group consisting of Ewing osteosarcoma, malignant melanoma, pancreatic carcinoma, prostate cancer (metastasis of a subclavicular lymph node), colorectal adenocarcinoma, and osteosarcoma.

(20) A process for preparing a compound of formula V

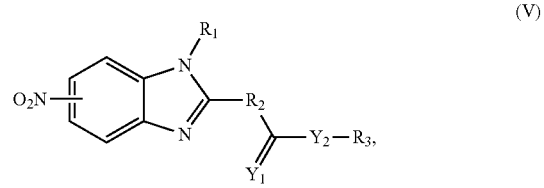

or an acid addition salt thereof, wherein $R_1$ represents alkyl, aryl or alkylaryl; $R_2$ represents alkanediyl, arylene, alkylarylene or arylalkanediyl; and $R_3$ represents H, alkyl, aryl or alkylaryl; $Y_1$ and $Y_2$ independently from each other represent oxygen or sulphur, wherein the nitro group is attached at position 4, 6 or 7 of the benzimidazole ring structure, or an acid addition salt thereof, in which process a compound of formula II

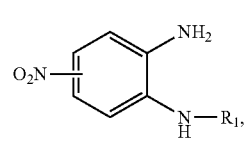

wherein $R_1$ is defined as above, and the nitro group is attached to any one of positions 3, 4 and 6 of the aniline moiety, when $R_3$ represents alkyl, aryl or alkylaryl, is reacted with a compound of formula III[1]

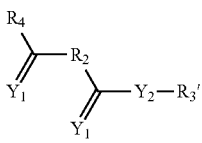

wherein $R_2$, $Y_1$ and $Y_2$ are defined as above, $R_3'$ represents alkyl, aryl or alkylaryl and $R_4$ is selected from the group consisting of —$Y_2$—H, chloro (—Cl) and —$Y_7$—$CY_1$—$R_2$—$CY_1$—$Y_2$—$R_3'$, or when $R_3$ represents H, compound of formula II is reacted with a compound of formula III² or a compound of formula III³

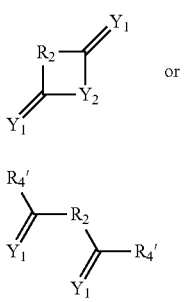

wherein $R_2$, $Y_1$ and $Y_2$ are defined as above, and $R_4'$ independently from each other represent —$Y_2$—H or chloro (—Cl), preferably both $R_4'$ represent —$Y_2$—H or one $R_4'$=—$Y_2$—H and the other $R_4'$=chloro (—Cl), more preferably both $R_4'$=—$Y_2$—H, with the proviso that in the case compound of formula III³ in which both $R_4'$=chloro, the chloro group which did not form an amide with amine compound of formula II is hydrolized in order to convert said chloro group to hydroxy group (—OH).

As regards the meaning of the terms "alkyl", "alkanediyl", "aryl(ene)", "alkylaryl(ene)" and "arylalkane (diyl)", reference is made to the explanations made under item (1) above. As regards the position of the nitro group at the benzimidazole ring of compound of formula (V), the explanations made for the bis(2-chloroethyl)amino group of compound of formula IX under item (1) likewise apply.

In compound of formula II, the nitro group is attached to any one of positions 3, 4 and 6 of the aniline moiety, as indicated in the following exemplary structural formula II'

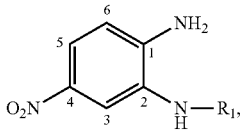

wherein the nitro group is in 4-position. Preferably, the nitro group is located at the 4 position of the aniline moiety of compound of formula II'.

Preferably, compound of formula III¹ or compound of formula III² is applied, more preferably compound of formula III².

(21) The process according to item (20), wherein said process is carried out without isolation of an intermediate compound of formula IV

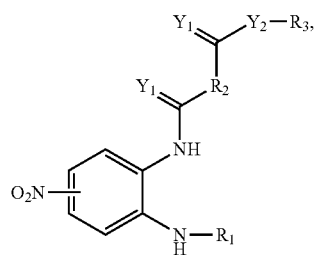

wherein $R_1$ represents alkyl, aryl or alkylaryl; $R_2$ represents alkanediyl, arylene, alkylarylene or arylalkanediyl; and $R_3$ represents H, alkyl, aryl or alkylaryl; $Y_1$ and $Y_2$ independently from each other represent oxygen or sulphur, or an acid addition salt thereof.

(22) The process according to item (20) or (21), wherein $R_1$ is C1-C3 alkyl, $R_2$ is C1-C3 alkanediyl, $R_3$ is H or C1-C3 alkyl, and $Y_1$ and $Y_2$ represent oxygen.

(23) The process according to any one of items (20) to (22), wherein $R_1$ is methyl, $R_2$ is propanediyl, $R_4$ is H or ethyl and $Y_1$ and $Y_2$ represent oxygen, preferably $R_1$ is methyl, $R_2$ is propanediyl, $R_3$ is ethyl and $Y_1$ and $Y_2$ represent oxygen.

(24) The process according to any one of items (20) to (23), wherein in compound of formula III¹, III² and III³, $Y_1$ and $Y_2$ represent oxygen; and/or $R_4$=—$Y_2$—$CY_1$—$R_2$—$CY_1$—$Y_2$—$R_3'$.

Preferably, compound of formula III² is glutaric anhydride having the structural formula

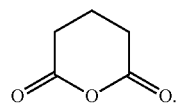

(25) The process according to any one of items (20) to (24), wherein compound of formula V'

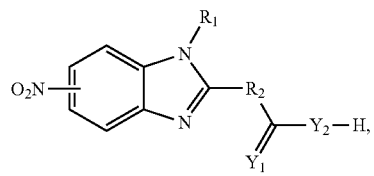

wherein $R_1$ represents alkyl, aryl or alkylaryl; $R_2$ represents alkanediyl, arylene, alkylarylene or arylalkanediyl; $Y_1$ and $Y_2$ independently from each other represent oxygen or sulphur, wherein the nitro is attached at position 4, 6 or 7 of the benzimidazole ring structure, or an acid addition salt thereof, is further converted to compound of formula V'''

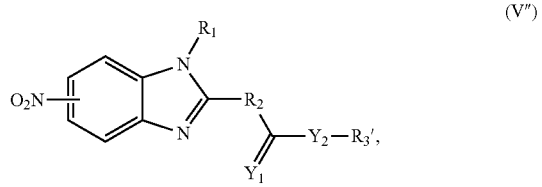

wherein $R_1$, $R_2$, $Y_1$, $Y_2$ and the position of the nitro group are defined as above, and $R_3'$ represents alkyl, aryl or alkylaryl, or an acid addition salt thereof, by means of transesterification with an alcohol of formula $R_3'$—OH, wherein $R_3'$ is defined as above.

(26) The process according to item (25), wherein transesterification is carried out in the presence of a proton donor, preferably an inorganic proton donor, more preferably an inorganic proton donor selected from the group consisting of hydrohalogen acid and sulphuric acid ($H_2SO_4$), even more preferably HCl or $H_2SO_4$, in particular $H_2SO_4$.

The term "proton donor" as used herein means a Brønsted acid which provides for donating proton(s).

(27) The process according to item (25) or (26), wherein $R_3'$ is C1-C3 alkyl, preferably ethyl.

(28) A process for preparing a compound of formula IX, VIII or VII according to any one of items (1) to (18), which process comprises the steps of:
a) preparing a compound of formula V according to a process of any one of items (20) to (27), and
b) further converting compound of formula V to any one of compounds of formula IX, VIII or VII.

As regards the meaning of the terms "alkyl", "alkanediyl", "aryl(ene)", "alkylaryl(ene)", and "arylalkane (diyl)" and the position of the bis(2-chloroethyl)amino group at the benzimidazole ring of compound of formula IX, reference is made to the explanations made under item (1) above.

As regards the position of the bis(2-chloroethyl)amino group at the benzimidazole ring of compound of formula VIII, the explanations made for the bis(2-chloroethyl)amino group of compound of formula IX under item (1) likewise apply.

(29) A pharmaceutical composition comprising compound of formula IX and/or VIII according to any one of items (1) to (7) and (9) to (18) in the form of their free acid/base or a pharmaceutically acceptable salt thereof as a pharmaceutically active agent(s) and at least one pharmaceutically acceptable excipient.

The term "pharmaceutically active agent" as used herein means any active pharmaceutical ingredient intended for treatment or prophylaxis of a disease of a subject to be treated, specifically mammals such as humans. In general it means any active pharmaceutical ingredient that has an effect on the physiological conditions of the subject.

The term "pharmaceutically acceptable excipient" as used herein means any physiologically harmless or inert, pharmacologically inactive material compatible with the physical and chemical characteristics of the active agent. Suitable pharmaceutically acceptable excipients are generally known in the art.

(30) The pharmaceutical composition according to item (29) for oral and/or parenteral administration.

DETAILED DESCRIPTION OF THE INVENTION

The present invention is now described in more detail by referring to further preferred and further advantageous embodiments and examples, which are, however, presented for illustrative purposes only and shall not be understood as limiting the scope of the present invention.

According to one aspect of the invention, highly desirable compounds derived from bendamustine analogues are provided in the form of compound of formula IX

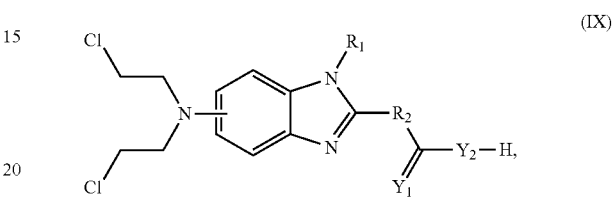

or a salt thereof, wherein $R_1$ is alkyl, aryl or alkylaryl; $R_2$ represents alkanediyl, arylene, alkylarylene or arylalkanediyl; $Y_1$ and $Y_2$ independently from each other represent oxygen or sulphur, wherein the bis(2-chloroethyl)amino group is attached at position 4, 6 or 7 of the benzimidazole ring structure.

It was surprisingly found by the present invention that the novel 4, 6 or 7 positions of the N-lost moiety in the iso-bendamustine derivatives of compound of formula IX provide for a beneficial alteration of both electronic as well as steric effects compared to conventional bendamustine in which the N-lost moiety is in 5-position of the benzimidazole ring structure. Without wishing to be bound to theory, it is believed that these altered electronic and/or steric effects provide for a good or even an improved antiproliferative potency of compound of formula IX compared to conventional bendamustine (HCl). Furthermore, antiproliferative potency and further useful properties may be additionally fine-tuned and eventually improved by suitable selections for substituents $R_1$, $R_2$, $Y_1$ and $Y_2$.

According to another aspect of the invention, compounds of formula VII or VIII

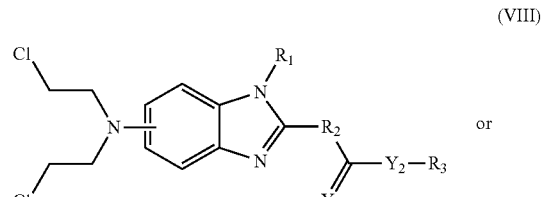

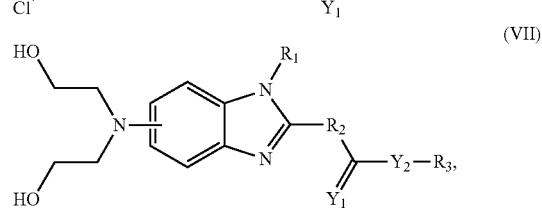

or (pharmaceutically acceptable) acid addition salts thereof, are provided, wherein $R_1$ and $R_3$ are independently from each other selected from alkyl, aryl or alkylaryl; $R_2$ represents alkanediyl, arylene, alkylarylene or arylalkanediyl; $Y_1$ and $Y_2$ independently from each other represent oxygen or sulphur, wherein the bis(2-chloroethyl)amino group or the bis(2-hydroxyethyl)amino group is attached at position 4, 6 or 7 of the benzimidazole ring structure; optionally, $R_3$ is substituted with an amine moiety —$NR_5R_6$ in which $R_5$ and $R_6$ independently from each other represent substituted or unsubstituted alkyl or $R_5$ and $R_6$ together represent a C3-C7 alkyl chain forming a 4- to 8-membered ring structure together with the nitrogen located between $R_5$ and $R_6$, wherein one or more carbon atoms in said ring structure is/are optionally replaced by (a) heteroatom(s) selected from the group consisting of nitrogen (N), oxygen (O) or sulphur (S).

As regards compounds of formula VIII, without wishing to be bound to theory, it is believed that these compounds exhibit a good or even an improved antiproliferative potency compared to conventional bendamustine. In particular, it is believed that the ester compounds of formula VIII provide for an improved cellular uptake compared with bendamustine in form of the free acid owing to an improved combination of solubility in aqueous medium and increased passage through cell membranes compared with bendamustine (HCl). Hence, compounds of formula VIII represent valuable active pharmaceutical ingredients with a better administration (oral, parenteral).

Compounds of formula VII represent valuable intermediate compounds for preparing active pharmaceutical ingredients such as iso-bendamustine derivatives.

According to a preferred embodiment, any one of compounds of formulae IX, VIII and VII may be advantageously structurally modified by structural modifications (A) to (C), respectively alone or in combination:

(A) $R_1$ is C1-C6 alkyl, $R_2$ is C1-C6 alkanediyl, and $Y_1$ and $Y_2$ represent oxygen; preferably $R_1$ is C1-C4 alkyl, $R_2$ is C1-C4 alkanediyl, and $Y_1$ and $Y_2$ represent oxygen;

(B) $R_1$ is C1-C3 alkyl, $R_2$ is C1-C3 alkanediyl, and $Y_1$ and $Y_2$ represent oxygen; and (C) $R_1$ is methyl, $R_2$ is propanediyl, and $Y_1$ and $Y_2$ represent oxygen.

Thereby, particularly suitable selections are determined for substituents $R_2$, $Y_1$ and $Y_2$.

According to another preferred embodiment, in compounds of formula VIII and VII, $R_3$ is C1-C3 alkyl, preferably ethyl. In this way, a particularly suitable selection for $R_3$ is determined.

According to a further preferred embodiment, in compounds of formulae VIII and VII, $R_3$ is substituted with an amine moiety —$NR_5R_6$. Preferably, said amine moiety is in the form of a ring structure formed by $R_5$ and $R_6$ together with the nitrogen located between $R_5$ and $R_6$ has at least one of the following structural characteristics (i) to (v), respectively alone or in combination:

(i) one carbon atom is replaced by one nitrogen atom or one oxygen atom, preferably one oxygen atom;

(ii) a further nitrogen atom is substituted (—$NR_7$—) or unsubstituted (—NH—), preferably substituted with $R_7$ selected from the group consisting of alkyl, aryl, alkylaryl or arylalkyl, more preferably with alkyl;

(iii) the ring structure is in the form of a 5- or 6-membered ring, preferably a 6-membered ring;

(iv) the ring structure is selected from the group consisting of pyrrolidine, piperidine, piperazine and morpholino, preferably piperazine or morpholino.

(v) the atoms of the ring structure may be unsubstituted, or substituted with a substituent selected from the group consisting of C1-C4 alkyl, C1-C4 alkoxy, C1-C4 alkylsulfide, unsubstituted amino (—$NH_2$), dialkylamino in which alkyl is C1-C4 alkyl; preferably C1-C4 alkyl or C1-C4 alkoxy; more preferably the ring structure is unsubstituted.

Without wishing to be bound to theory, it is believed that structural modifications (i) to (v) provide for particularly advantageous modifications in terms of solubility in aqueous solution and efficacy in terms of cytotoxicity.

According to a particular embodiment of the present invention, compounds of formulae VIII and IX in the form of their free acid/base or a pharmaceutically acceptable salt thereof may be used as a medicament for the therapeutic treatment of diseases selected from the group consisting of acute T cell leukaemia (Jurkat, T1 B-152), Erythroleukemia (HEL 92.1.7, T113-180), Ewing osteosarcoma (SK-ES1, HTB-86), (hormone dependent) mamma carcinoma (MCF-7, HTB-22), cervix carcinoma (multidrug resistant KB-V1), colorectal cancer, medulloblastoma (Daoy, HTB-186), glioblastoma (U-118MG, HTB-15; LN-18, CRL-2610) and astrocytoma (SW1783, HTB-13), malignant melanoma (SK-Mel3, HTB-69), histocytic lymphoma (U-937; CRL-1593.2), pancreatic carcinoma (Capan-1, HTB-80), prostate cancer (metastasis of a subclavicular lymph node) (LnCap clone FGC, CRL-1740), large cell bronchial carcinoma (NCIH460, HTB-177), colorectal adenocarcinoma (HT-29, HTB-38), osteosarcoma (MG-63, CRL-1427), wherein the acronyms in brackets designate the cell line and the corresponding ATCC-number representative of the respective cancer entities.

As an example, the synthesis of 6-iso-bendamustine isomer of formula IX''' starting from compound of formula VII'' is illustrated in Scheme 1 below:

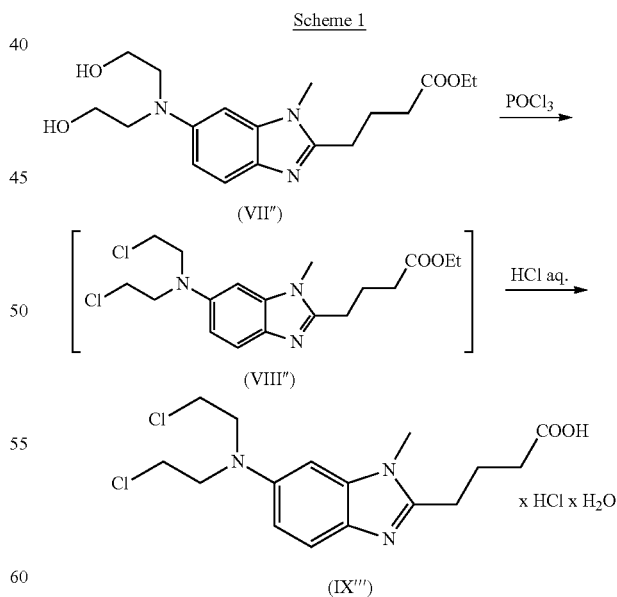

As can be gathered from Scheme 1, compound of formula VII'' may be converted to compound of formula VIII'' by means of chlorination, using e.g. phosphorous oxychloride as chlorinating agent, and in a subsequent step, compound of formula VIII'' is subjected to ester cleavage by means of e.g.

aqueous HCl in order to obtain 6-iso-bendamustine hydrochloride hydrate of compound of formula IX'''.

The precursor compound of formula VII" can be efficiently prepared, for example by means of the synthetic pathway starting from the readily available starting material 4-nitrobenzene-1,2-diamine (compound of formula I", as depicted in Scheme 2 below:

Scheme 2

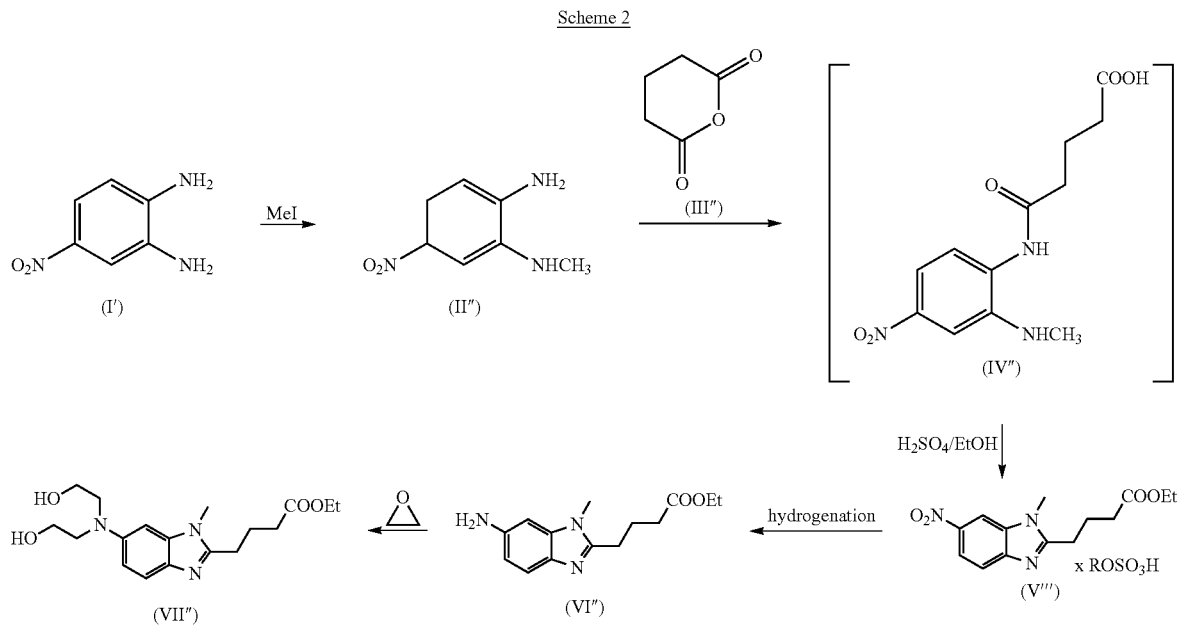

According to another aspect of the invention, a process is provided for preparing a compound of formula V

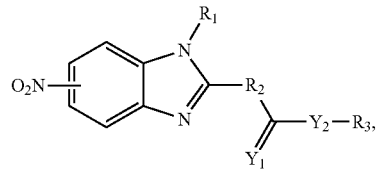

or an acid addition salt thereof,
wherein $R_1$ represents alkyl, aryl or alkylaryl; $R_2$ represents alkanediyl, arylene, alkylarylene or arylalkanediyl; and $R_3$ represents H, alkyl, aryl or alkylaryl; $Y_1$ and $Y_2$ independently from each other represent oxygen or sulphur, wherein the nitro group is attached at position 4, 6 or 7 of the benzimidazole ring structure, or an acid addition salt thereof, in which process a compound of formula II

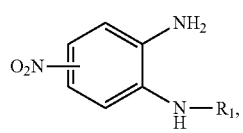

wherein $R_1$ is defined as above, and the nitro group is attached to any one of positions 3, 4 and 6 of the aniline moiety,
when $R_3$ represents alkyl, aryl or alkylaryl, is reacted with a compound of formula III$^1$

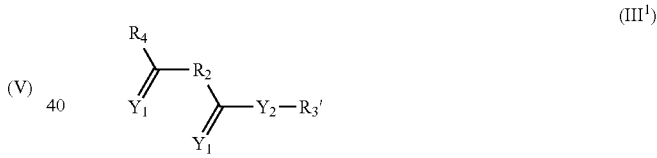

wherein $R_2$, $Y_1$ and $Y_2$ are defined as above, $R_3'$ represents alkyl, aryl or alkylaryl and $R_4$ is selected from the group consisting of —$Y_2$—H, chloro (—Cl) and —$Y_2$—$CY_1$—$R_2$—$CY_1$—$Y_2$—$R_3'$,
or when $R_3$ represents H, compound of formula II is reacted with a compound of formula III$^2$ or a compound of formula III$^3$

wherein $R_2$, $Y_1$ and $Y_2$ are defined as above, and $R_4'$ independently from each other represent —$Y_2$—H or chloro (—Cl), preferably both $R_4'$ represent or one $R_4'$=—$Y_2$—H and the other $R_4'$=chloro (—Cl), more preferably both $R_4'$=—$Y_2$—H,
with the proviso that in the case compound of formula $III^3$ in which both $R_4'$=chloro, the chloro group which did not form an amide with amine compound of formula II is hydrolized in order to convert said chloro group to hydroxy group (—OH).

It was surprisingly found by the inventors that compound of formula II readily forms an imidazole structure of compound of formula V when it is reacted with a compound of formula $III^1$, $III^2$ or $III^3$. In particular, the nitro group in 3, 4 and 6 position of compound of formula II provides for a significantly improved reactivity of the amino group of compound of formula II compared to e.g. $N^2$-methyl-4-nitro-1,2-diamine having the structural formula (in which the positions of the benzene ring are indicated with the respective numbers)

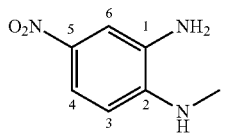

which is typically applied as the starting material for synthesizing the benzimidazole moiety of conventional bendamustine. However, when reacting $N^2$-methyl-4-nitro-1,2-diamine with glutaric anhydride, due to the relative poor reactivity of $N^2$-methyl-4-nitro-1,2-diamine, no benzimidazole ring structure is formed, rather, an amide compound having the structural formula

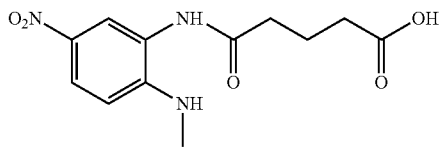 [SMILES: CNc1ccc([N+](=O)[O-])cc1NC(=O)CCCC(=O)O]

is isolated, as can be gathered e.g. from prior art documents DD 34727 and J. Chen et al., Org. Process Res. Dev. 2011, 15, p. 1063-1072. In contrast to the aforementioned prior art process, the present process renders possible to dispense with isolation of an intermediate amide compound, rather, owing to the improved reactivity of compound of formula II due to electronic and/or steric effects imparted by the nitro group in 3, 4 and 6 position of the aniline moiety, imidazole compound of formula V can be directly obtained. This finding suggests that—compared to conventional bendamustine—electronic as well as steric effects will become significant also in terms of pharmacological activity and optionally further properties of a compound of formula IX prepared from compound of formula V.

According to yet another aspect of the present invention, a process for preparing a compound of formula IX, VIII or VII according to any one of items (1) to (11) is provided, which process comprises the steps of:
  a) preparing a compound of formula V according to a process of any one of items (13) to (20), and
  b) further converting compound of formula V to any one of compounds of formula IX, VIII or VII.

As regards this aspect of the invention, owing to the introduction of a substituent convertible to a N-lost group (bis(2-chloroethyl)amino) at position 4, 6 or 7 of the benzimidazole ring structure of compound of formula V at an early stage of the synthetic pathway, subsequent reaction steps for converting compound of formula V to a bendamustine isomer of compound of formula IX can be carried out analogously to reaction steps known in prior art for the preparation of conventional bendamustine. That is, said subsequent reaction steps do not require laborious modifications of reaction conditions and/or reaction pathway.

According to another aspect of the invention, a pharmaceutical composition is provided which comprises compound of formula IX and/or compound of formula VIII in the form of their free acid/base or a pharmaceutically acceptable salt thereof as a pharmaceutically active agent(s) and at least one pharmaceutically acceptable excipient.

Preferably, suitable pharmaceutically acceptable excipient(s) is/are selected from the group consisting of binders, disintegrants, bulk polymers, glidants, lubricants and preservatives, without being limited thereto.

The term "binder" as used herein means a binding agent which improves adhesion in between particles of the pharmaceutically active agent.

The term "disintegrant" as used herein means an agent providing for rapid disintegration of a pharmaceutical composition into smaller fragments when in contact with water, wherein dissolution of the pharmaceutical composition and, in particular, of a pharmaceutically active agent comprised therein is improved.

The term "bulk polymer" as used herein means a polymeric filling agent, which is typically added to a pharmaceutical composition in suitable amounts.

The term "glidants and lubricants" as used herein means components acting as formulation and processing aids.

The term "preservatives" as used herein means a substance or mixture of substances which prevents decomposition of a pharmaceutical composition, e.g. microbial or bacterial decomposition.

The following examples further illustrate the invention. They are provided for illustrative purposes only and are not intended to limit the invention in any way. The examples and modifications or other equivalents thereof will become apparent to those versed in the art in the light of the present entire disclosure.

EXAMPLES

Example 1: $N^2$-methyl-4-nitrobenzene-1,2-diamine (II')

$N^2$-methyl-4-nitrobenzene-1,2-diamine having the structural formula

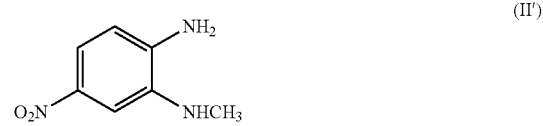 [SMILES: CNc1cc([N+](=O)[O-])ccc1N]

was prepared as follows:

A 500 mL round bottom flask was charged with 4-nitrobenzene-1,2-diamine (40.0 g, 260 mmol), methyl iodide (13 mL, 210 mmol) and DMF (300 mL). Saturated sodium carbonate solution (60 mL) was added with stirring and the mixture was stirred for 18 hours. After filtration the solution was concentrated to dryness in vacuum and the residue was purified by flash column chromatography (ethyl acetate/heptanes=7:3) to afford $N^2$-methyl-4-nitrobenzene-1,2-diamine in the form of a red oil. Yield: 27.9 g (63%).

$^1$H NMR (500 MHz, DMSO-d6): δ=7.50 (dd, 1H, $^4J$=2.8 Hz, $^3J$=8.7 Hz, H-4), 7.10 (d, 1H, $^4J$=2.8 Hz, H-6), 6.55 (d, 1H, $^3J$=8.7 Hz, H-3), 6.12 (s, 2H, NH$_2$), 5.20 (q, 1H, $^3J$=5.0 Hz, NH), 2.78 (d, 3H, $^3J$=5.0 Hz, CH$_3$).

$^{13}$C NMR (126 MHz, DMSO-d6): δ=143.6, 137.2, 136.4 (C), 115.6, 110.5, 102.6 (CH), 29.8 (CH$_3$).

LC-MS (ESI$^-$): m/z=166 (M–H$^+$).

Example 2: Ethyl 4-(1-methyl-6-nitro-1H-benzimidazol-2-yl)butanoic Acid (V')

Ethyl 4-(1-methyl-6-nitro-1H-benzimidazol-2-yl)butanoic acid having the structural formula

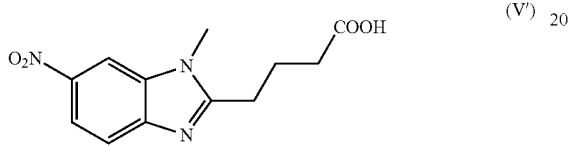

was prepared as follows:

$N^2$-Methyl-4-nitrobenzene-1,2-diamine (9.65 g, 57.7 mmol) was mixed with ethyl acetate (170 ml) and glutaric anhydride (7.47 g, 65.4 mmol) was added. The mixture was heated to reflux for 5.5 h, and a yellow-orange precipitate was observed after 1 h from the orange reaction solution. Then the suspension was cooled on ice for 45 min, followed by vacuum filtration. The collected precipitate was washed with ice-cold EtOAc (3×5 ml) and ice-cold EtOH (2×5 ml) to yield 6.16 g (41%) of ethyl 4-(1-methyl-6-nitro-1H-benzimidazol-2-yl)butanoic acid in the form of a yellow solid.

$^1$H-NMR (DMSO): δ=8.52 (1H, d, J=2.2 Hz, Ar), 8.06 (1H, dd, J=8.8, 2.2 Hz, Ar), 7.71 (1H, d, J=8.8 Hz, Ar), 3.84 (3H, s, CH$_3$), 2.95 (2H, t, J 7.5 Hz, CH$_2$), 2.39 (2H, t, J 7.5 Hz, CH$_2$), 2.02 (2H, t, J 7.5 Hz, CH$_2$).

$^{13}$C-NMR (DMSO): δ=174.09, 160.67, 146.83, 142.02, 135.13, 118.31, 116.92, 106.87, 32.88, 29.96, 25.97, 21.72.

LC-MS (ESI$^+$): m/z=264.1 (M+H$^+$)

Example 3: Ethyl 4-(1-methyl-6-nitro-1H-benzimidazol-2-yl)butanoate Ethyl Sulfate (V'')

Ethyl 4-(1-methyl-6-nitro-1H-benzimidazol-2-yl)butanoate ethyl sulfate having the structural formula

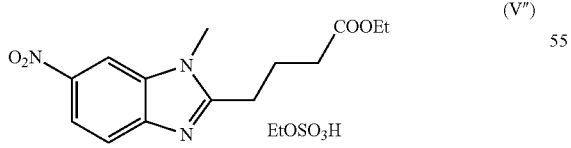

was prepared as follows:

5-{[2-(methylamino)-4-nitrophenyl]amino}-5-oxopentanoic acid (6.06 g, 23.09 mmol) was suspended in ethanol (40 ml) and heated to reflux. After 50 min, H$_2$SO$_4$ (1.82 ml, 34.07 mmol) was added over 15 min. The obtained solution was slowly cooled to 0° C. At 10° C., a thick suspension was obtained that was re-warmed to 40-43° C. and cooled again to 0° C. to get a better stirrable mixture. After stirring 30 min on ice, the suspension was vacuum-filtered and washed with ice-cold ethanol (3×5 ml) to yield 6.65 (69%) of ethyl 4-(1-methyl-6-nitro-1H-benzimidazol-2-yl)butanoate ethyl sulfate in the form of an off-white solid.

Example 4: Ethyl 4-(1-methyl-6-nitro-1H-benzimidazol-2-yl)butanoate (V''')

Ethyl 4-(1-methyl-6-nitro-1H-benzimidazol-2-yl)butanoate having the structural formula

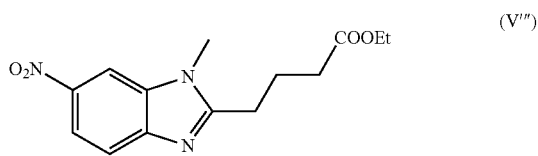 [SMILES: CCOC(=O)CCCc1nc2ccc([N+](=O)[O-])cc2n1C]

was prepared as follows:

Ethyl 4-(1-methyl-6-nitro-1H-benzimidazol-2-yl)butanoate ethyl sulfate (6.60 g, 15.8 mmol) was suspended in water (330 ml). NaOH (50%, 2.04 g) was diluted with water (10 ml) and added over 10 min. The suspension was stirred for 1 h at r.t. and vacuum-filtered (washed with water (2×10 ml). After drying at 60° C. for 1 h, 4.23 g (92%) of free base of ethyl 4-(1-methyl-6-nitro-1H-benzimidazol-2-yl)butanoate was obtained in the form of an off-white powder.

$^1$H-NMR (DMSO): δ=8.54 (1H, d, J=2.2 Hz, aromatic), 8.07 (1H, dd, J=8.9, 2.2 Hz, aromatic), 7.72 (1H, d, J=8.9 Hz, aromatic), 4.05 (2H, q, J=7.1 Hz, COOC$\underline{H}_2$CH$_3$), 3.85 (3H, s, CH$_3$), 2.97 (2H, t, J=7.5 Hz, CH$_2$), 2.49 (2H, t, J=7.5 Hz, CH$_2$), 2.06 (2H, pent, J=7.5 Hz, CH$_2$), 1.17 (3H, t, J=7.1 Hz, COOCH$_2$C$\underline{H}_3$).

$^{13}$C-NMR (DMSO): δ=172.42, 160.47, 146.79, 142.01, 135.11, 118.29, 116.88, 106.85, 59.72, 32.65, 29.93, 25.83, 21.57, 14.00.

LC-MS (ESI$^+$): m/z=292.1 (M+H$^+$)

Example 5: Ethyl 4-(6-amino-1-methyl-1H-benzimidazol-2-yl)butanoate (VI'')

Ethyl 4-(6-amino-1-methyl-1H-benzimidazol-2-yl)butanoate having the structural formula

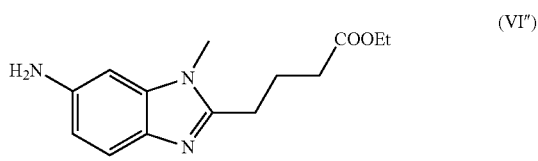

was prepared as follows:

A hydrogenation reactor was charged with ethyl 4-(1-methyl-6-nitro-1H-benzimidazol-2-yl)butanoate (4.2 g, 14.4 mmol) and ethanol (300 ml). After complete dissolution and inertisation of the vessel, Pd on activated charcoal catalyst (5%, moist, 340 mg) was added and hydrogenation (4.5 bar, 60° C.) was performed for 4 h (no further H$_2$ consumption). The catalyst was removed by filtration and after evaporation of the solvent, 4.0 g of crude ethyl 4-(6-amino-1-methyl-1H-benzimidazol-2-yl)butanoate was obtained and was subsequently recrystallized from ethanol (20 ml). 2.73 g (72.5%) and additional 0.87 g (23%) from the mother liquor of the recrystallisation step were obtained after drying in vacuum (40° C.).

$^1$H-NMR (DMSO): δ=7.18 (1H, d, J=8.4 Hz, aromatic), 6.51 (1H, d, J=1.8 Hz, aromatic), 6.46 (1H, dd, J=8.4, 1.8 Hz, aromatic), 4.85 (2H, s, NH$_2$), 4.05 (2H, q, J=7.1 Hz, COOC$\underline{H}_2$CH$_3$), 3.54 (3H, s, CH$_3$), 2.77 (2H, t, J=7.4 Hz, CH$_2$), 2.44 (2H, t, J=7.4 Hz, CH$_2$), 1.97 (2H, pent, J=7.4 Hz, CH$_2$), 1.17 (3H, t, J=7.1 Hz, COOCH$_2$C$\underline{H}_3$).

$^{13}$C-NMR (DMSO): δ=172.57, 151.23, 144.14, 136.79, 134.20, 118.27, 110.36, 93.09, 59.65, 32.76, 28.99, 25.51, 22.10, 14.01.

LC-MS (ESI$^+$): m/z=262.2 (M+H$^+$)

Example 6: Ethyl 4-{6-[bis(2-hydroxyethyl)amino]-1-methyl-1H-benzimidazol-2-yl}butanoate (VII″)

Ethyl 4-{6-[bis(2-hydroxyethyl)amino]-1-methyl-1H-benzimidazol-2-yl}butanoate having the structural formula

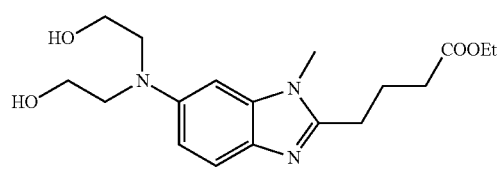

(VII″)

was prepared as follows:

Ethyl 4-(6-amino-1-methyl-1H-benzimidazol-2-yl)butanoate (1.0 g, 3.83 mmol) was dissolved in acetic acid (3.0 ml) and water (8.5 ml). Ethylene oxide gas was added into the solution in intervals for 4 h and stirred at r.t. for additional 15 h. A second feed of oxirane was performed and stirring was continued for another 6 h. The reaction was followed by TLC (10% methanol in DCM). After reaction, the reaction solution was added dropwise into a solution of K$_2$CO$_3$ (6 g) in water (20 ml) at 0-5° C. A suspension together with a compact amorphous solid was filtered, and the resulting filter cake was washed with water (2×10 ml) and dried overnight at 40° C. in a constant stream of air (1.21 g, 90%).

HPLC purity: 95.9% rel. area.

$^1$H NMR (500 MHz, DMSO-d$_6$, ppm): δ=7.30 (d, J=9.5 Hz, 1H, Arom. CH=CN), 6.63 (d, J=9.5 Hz, 1H, Arom. C$\underline{H}$=CN(CH$_2$CH$_2$OH)$_2$), 6.62 (s, 1H, Arom. C$\underline{H}$=CNMe), 4.75 (br s, 2H, OH), 4.05 (q, J=7.1 Hz, 2H, COOC$\underline{H}_2$CH$_3$), 3.61 (s, 3H, NCH$_3$), 3.57 (t, J=6.4 Hz, 4H, 2×CH$_2$N), 3.44 (t, J=6.4 Hz, 4H, 2×CH$_2$O), 2.80 (t, J=7.4 Hz, C$\underline{H}_2$-imidazole), 2.44 (t, J=7.4 Hz, CH$_2$COO), 1.9 (p, J=7.4 Hz, CH$_2$C$\underline{H}_2$CH$_2$), 1.18 (t, J=7.1 Hz, COOCH$_2$C$\underline{H}_3$)

$^{13}$C-{H}-NMR (125 MHz, DMSO-d$_6$, ppm): δ=172.58 (COO), 151.83 (NC=N), 144.41 ($\underline{C}$—N(CH$_2$CH$_2$OH)$_2$), 137.06 (Arom.), 133.83 (Arom.), 118.34 (Arom.), 108.14 (Arom.), 91.68 (Arom. (NMe)C$\underline{C}$HCN(CH$_2$CH$_2$OH)$_2$), 59.68 (NCH$_2$), 58.29 (OCH$_2$), 54.07 (COO$\underline{C}$H$_2$), 32.76 (probably NCH$_3$), 29.06 (probably $\underline{C}$H$_2$COO), 25.58 ($\underline{C}$H$_2$-imidazole), 22.12 (CH$_2\underline{C}$H$_2$CH$_2$), 14.03 (CH$_3$).

LC-MS (ESI$^+$): m/z=350.1 (M+H$^+$)

Example 7: 6-Iso-Bendamustine Ethylester (Denotation According to IUPAC-Nomenclature: ethyl 4-{6-[bis(2-chloroethyl)amino]-1-methyl-1H-benzimidazol-2-yl}butanoate) (VIII″)

6-iso-bendamustine ethylester having the structural formula

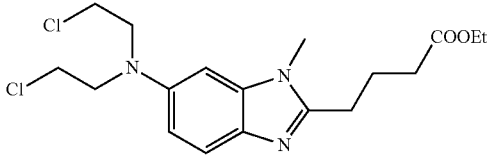

(VIII″)

was prepared as follows:

A round bottom flask equipped with a magnetic stirring bar and a reflux-condenser with oil ventile was charged with phosphorus oxychloride (2.0 mL, 21.9 mmol) and heated to an internal temperature of 65° C. Ethyl 4-{6-[bis(2-hydroxyethyl)amino]-1-methyl-1H-benzimidazol-2-yl}butanoate (1.0 g, 2.9 mmol) was added in portions within 13 min. After the addition was completed, the mixture was heated to reflux temperature and stirring was continued for a further 10 min. The mixture was allowed to reach room temperature and 1,2-dimethoxyethane (2.3 mL) was added with stirring.

A second round bottom flask was charged with potassium bicarbonate (10.7 g, 107 mmol) and potable water (13 mL). The product solution was added slowly with stirring to the bicarbonate within 20 min, maintaining an internal temperature of about 18 to 28° C. The suspension was diluted with potable water (10 mL), and 6-iso-bendamustine ethylester was isolated as a solid by means of filtration, washed with potable water (4×2.5 mL) and used in the next synthetic step without further purification.

Yield (moist): 1.73 g $^1$H NMR (500 MHz, DMSO-d$_6$, ppm): δ=7.37 (d, $^3$J=8.7 Hz, 1H, arom. H-4), 6.78 (expected $^4$J coupling not resolved, 1H, arom. H-7), 6.68 (d, $^3$J=8.7 Hz, expected $^4$J coupling not resolved, 1H, arom. H-5), 4.05 (q, $^3$J=7.0 Hz, 2H, OC$\underline{H}_2$CH$_3$), 3.75 (s, 8H, C$\underline{H}_2$C$\underline{H}_2$Cl), 3.65 (s, 3H, CH$_3$N), 2.82 (t, $^3$J=7.3 Hz, 2H, C$\underline{H}_2$—CH$_2$—CH$_2$-Ester), 2.44 (t, $^3$J=7.2 Hz, 2H, CH$_2$—CH$_2$—C$\underline{H}_2$-Ester), 1.99 (m, 2H, CH$_2$—C$\underline{H}_2$—CH$_2$-Ester), 1.18 (t, $^3$J=7.0 Hz, 3H, OC$\underline{H}_2$CH$_3$).

$^{13}$C-{$^1$H}-NMR (125 MHz, DMSO-d$_6$, ppm): δ=173.1 ($\underline{C}$OOEt), 153.3 (arom. CN$_2$), 143.0 (arom. $\underline{C}$N(CH$_2$CH$_2$Cl)$_2$), 137.6 (arom.), 135.5 (arom.), 119.3 (arom. C-4), 109.3 (arom. C-5), 94.0 (arom. C-7), 60.2 ($\underline{C}$H$_2$CH$_3$), 53.7 (N($\underline{C}$H$_2$CH$_2$Cl)$_2$), 42.0 (N(CH$_2\underline{C}$H$_2$Cl)$_2$), 33.3 (CH$_2$—CH$_2$—$\underline{C}$H$_2$-Ester), 29.8 (CH$_3$), 26.1 ($\underline{C}$H$_2$—CH$_2$—CH$_2$-Ester), 22.6 (CH$_2$—$\underline{C}$H$_2$—CH$_2$-Ester), 14.6 (CH$_2\underline{C}$H$_3$).

HPLC-purity: 94.1% relative area

LC-MS (ESI$^+$): m/z=386.0 (M+H$^+$; 100% relative intensity)

Example 8: 6-iso-bendamustine Hydrochloride Containing about 3.8 Wt.-% of Water (Denotation According to IUPAC-Nomenclature: 4-{6-[bis(2-chloroethyl)amino]-1-methyl-1H-benzimidazol-2-yl}butanoic Acid Hydrochloride) (IX''')

6-iso-bendamustine hydrochloride having the structural formula

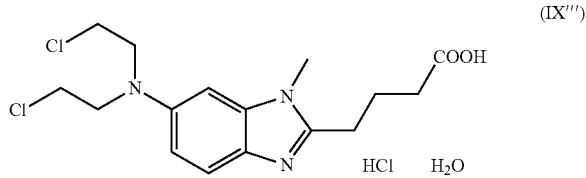 [SMILES: Cn1c(CCCC(=O)O)nc2ccc(N(CCCl)CCCl)cc21 ; Cl ; O]

(IX''')

containing about 3.8 wt.-% of water was prepared as follows:

A round bottom flask was charged with the crude 6-iso-bendamustine ethyl ester (1.5 g, moist product) and hydrochloric acid (37%, 5.0 mL). The solution was concentrated with a rotary evaporator at 60° C. bath temperature under reduced pressure during 4 h. The viscous concentrate was allowed to cool down to about 38° C. and reverse osmosis water (10 mL) was added. Vigorous stirring of the mixture yielded an emulsion which solidified upon scratching the glass wall of the vessel. Stirring was continued for a further 15 min at ambient temperature and the precipitate was isolated by filtration, washed with reverse osmosis water (3×0.4 mL) to yield 6-iso-bendamustine hydrochloride in the form of a colorless solid containing about 3.8 wt.-% of water after drying over night in a constant stream of air.

Yield: 0.54 g (46%)

$^1$H NMR (500 MHz, DMSO-$d_6$, ppm): δ=16-14 (s, br, 0.7H, acidic), 13-11 (s, br, 0.7H, acidic), 7.57 (d, $^3$J=9.1 Hz, 1H, arom. H-4), 7.11 (d, $^4$J=1.7 Hz, 1H, arom. H-7), 7.07 (dd, $^3$J=9.1 Hz, $^4$J=1.7 Hz, 1H, arom. H-5), 3.90 (s, 3H, CH$_3$N), 3.86 (t, $^3$J=6.7 Hz, 4H, 2×NC$\underline{H}_2$CH$_2$Cl), 3.80 (t, $^3$J=6.7 Hz, 4H, NCH$_2$C$\underline{H}_2$Cl), 3.16 (t, $^3$J=7.6 Hz, 2H, C$\underline{H}_2$—CH$_2$—CH$_2$—COOH), 2.41 (t, $^3$J=7.2 Hz, 2H, CH$_2$—CH$_2$—C$\underline{H}_2$—COOH), 2.02 (m, 2H, CH$_2$—C$\underline{H}_2$—CH$_2$—COOH); acidic protons diminished in intensity, presumably due to solvent exchange.

$^{13}$C-{$^1$H}-NMR (125 MHz, DMSO-$d_6$, ppm): δ=174.1 (COOH), 152.1 (arom. $\underline{C}$N$_2$), 145.8 (arom. $\underline{C}$N(CH$_2$CH$_2$Cl)$_2$), 134.7 (arom.), 122.3 (arom.), 115.0 (arom. C-4), 113.1 (arom. C-5), 94.5 (arom. C-7), 53.0 (N($\underline{C}$H$_2$CH$_2$Cl)$_2$), 41.7 (N(CH$_2$$\underline{C}$H$_2$Cl)$_2$), 33.0 (CH$_2$—CH$_2$—$\underline{C}$H$_2$—COOH), 31.3 (CH$_3$), 24.0 ($\underline{C}$H$_2$—CH$_2$—CH$_2$—COOH), 21.7 (CH$_2$—$\underline{C}$H$_2$—CH$_2$—COOH).

IR (KBr): see spectrum; wavenumber=1719 (COOH)

Water content by Karl-Fischer-titration: 3.8% (calculated water content for 6-iso-bendamustine hydrochloride containing one molecule of water per molecule: 4.4%)

Chloride content by titration: 8.5% (calculated chloride content for monohydrochloride: 8.6%)

HPLC-purity: 98.6% relative area

NMR-purity: >99% (calculated for 6-iso-bendamustine HCl H$_2$O)

LC-MS (ESI$^+$): see TIC and spectrum; m/z=358.1 (M−Cl$^-$−H$_2$O; 100% relative intensity)

Melting point (not corrected): 174-176.5° C. (conducted manually with a melting point microscope; intermediate melting/re-crystallization was not visible)

DSC (heating rate: 10 K/min): first melting peak at 112.4° C. (onset: 106.1° C.); a re-crystallization minimum at 119.8° C. (onset: 117.1° C.); a second melting peak at 187.7° C. (onset: 185.2° C.)

Powder X-ray diffraction (XRD) data of the ten most intense signals (2θ and D values rounded to the second decimal place, I/I$_0$ values are rounded to first decimal place):

| entry | 2θ [°] | D [Å$^{-1}$] | I/I$_0$ |
| --- | --- | --- | --- |
| 1 | 7.83 | 11.29 | 231.7 |
| 2 | 10.01 | 8.83 | 157.3 |
| 3 | 13.18 | 6.71 | 94.9 |
| 4 | 13.75 | 6.43 | 97.0 |
| 5 | 14.96 | 5.92 | 161.3 |
| 6 | 15.34 | 5.77 | 150.0 |
| 7 | 18.47 | 4.80 | 397.7 |
| 8 | 22.27 | 3.99 | 1000.0 |
| 9 | 24.63 | 3.61 | 301.8 |
| 10 | 26.53 | 3.36 | 268.7 |

The invention claimed is:

1. A compound of formula IX in the form of a salt,

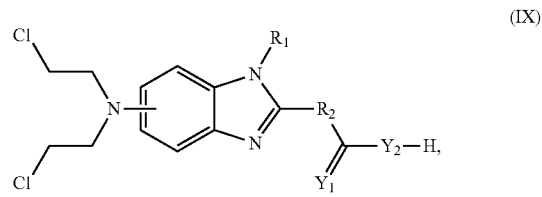

(IX)

wherein:
R$_1$ is alkyl, aryl or alkylaryl;
R$_2$ represents alkanediyl, arylene, alkylarylene or arylalkanediyl;
Y$_1$ and Y$_2$ independently represent oxygen, and
wherein the bis(2-chloroethyl)amino group is attached at position 6 of the benzimidazole ring structure,
wherein the salt comprises 0.6 to 1.4 mol water relative to 1 mol of the compound.

2. The compound of formula IX according to claim 1, wherein the compound is in the form of a hydrate.

3. The compound of formula IX according to claim 1, wherein the salt comprises 0.8 to 1.2 mol water relative to 1 mol of the compound.

4. The compound of formula IX according to claim 1, wherein the compound is in form of a base addition salt in which the base is selected from the group consisting of magnesium hydroxide, calcium hydroxide, zinc hydroxide, potassium hydroxide, sodium hydroxide, potassium carbonate, sodium carbonate, potassium hydrogen carbonate, sodium hydrogen carbonate, diethylamine, triethylamine, ethanolamine (2-aminoethanol), diethanolamine (2,2'-iminobis(ethanol)), triethanolamine (2,2',2"-nitrilotris(ethanol)), ethylenediamine, piperazine, piperidine, pyrrolidine, pyridine, morpholine, 1H-imidazole, N-methyl-glucamine, L-lysine, choline, L-arginine, benethamine, 4-(2-hydroxyethyl)-morpholine, tromethamine, 2-(dimethylamino) ethanol (Deanol), 1-(2-hydroxyethyl)-pyrrolidine, 2-(diethylamino)-ethanol, benzathine, hydrabamine, and betaine.

5. The compound according to claim 1, wherein:
R$_1$ is C$_1$-C$_6$ alkyl, and R$_2$ is C$_1$-C$_6$ alkanediyl.

6. The compound of formula IX according to claim 1, wherein the compound is in the form of an acid addition salt in which the acid is selected from the group consisting of hydrochloric acid, hydrobromic acid, sulfuric acid, phosphoric acid, glutamic acid, (+)-L-tartaric acid, citric acid, (−)-L-malic acid, DL-lactic acid, L-ascorbic acid, succinic acid, adipic acid, acetic acid, stearic acid, carbonic acid, thiocyanic acid, glycerol-phosphoric acid, L-aspartic acid, maleic acid, fumaric acid, galactaric acid, D-glucuronic acid, glycolic acid, D-glucoheptonic acid, hippuric acid, D-gluconic acid, glutaric acid, sebacic acid, capric (decanoic) acid, lauric acid, palmitic acid, alginic acid, benzoic acid, nicotinic acid, propionic acid, caprylic (octanoic) acid, naphthalene-1,5-disulfonic acid, ethane-1,2-disulfonic acid, cyclamic acid, p-toluenesulfonic acid, methanesulfonic acid, dodecylsulfuric acid, naphthalene-2-sulfonic acid, benzenesulfonic acid, oxalic acid, 2-hydroxy ethanesulfonic acid, ethanesulfonic acid, pannoic (embonic) acid, 2-oxoglutaric acid, 1-hydroxy-2-naphthoic acid, malonic acid, gentisic acid, lactobionic acid, (−)-L-pyroglutamic acid, oleic acid, (+)-camphoric acid, isobutyric acid, and orotic acid.

7. A process for preparing a compound of formula IX in the form of a salt,

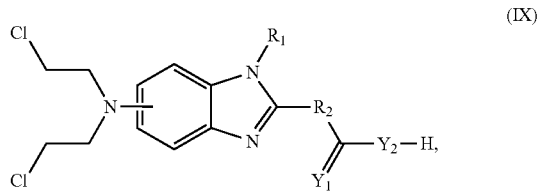

wherein $R_1$ is alkyl, aryl or alkylaryl; $R_2$ represents alkanediyl, arylene, alkylarylene or arylalkanediyl; $Y_1$ and $Y_2$ independently represent oxygen, and wherein the bis(2-chloroethyl)amino group is attached at position 6 of the benzimidazole ring structure, wherein the salt comprises 0.6 to 1.4 mol water relative to 1 mol of the compound, the process comprising the steps of:
preparing a compound of formula V or an acid addition salt thereof

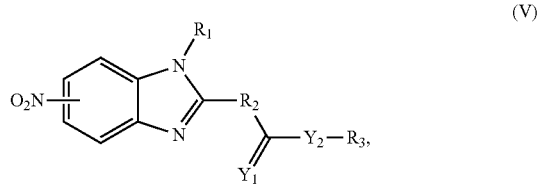

wherein $R_1$ represents alkyl, aryl or alkylaryl; $R_2$ is alkanediyl, arylene, alkylarylene or arylalkanediyl; and $R_3$ represents H, alkyl, aryl or alkylaryl; $Y_1$ and $Y_2$ independently represent oxygen, wherein the bis(2-chloroethyl)amino group is attached at position 6 of the benzimidazole ring structure, or an acid addition salt thereof, in which process a compound of formula II

wherein $R_1$ is defined as above, and the nitro group is attached to any one of positions 3, 4 and 6 of the aniline moiety, when $R_3$, represents alkyl, aryl or alkylaryl, is reacted with a compound of formula $III^1$

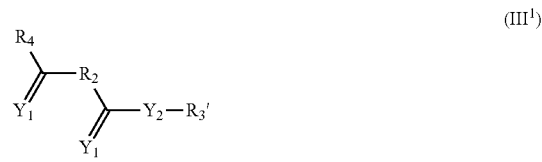

wherein $R_2$, $Y_1$ and $Y_2$ are defined as above, $R_3'$ represents alkyl, aryl or alkylaryl, and $R_4$ is selected from the group consisting of —$Y_2$—H, chloro (—Cl) and —$Y_2$—$CY_1$—$R_2$—$CY_1$—$Y_2$—$R_3'$;

or when $R_3$ represents H, compound of formula II is reacted with a compound of formula $III^2$ or a compound of formula $III^3$

wherein $R_2$, $Y_1$ and $Y_2$ are defined as above, and $R_4'$ independently from each other represent —$Y_2$—H or chloro (—Cl), particularly both $R_4'$ represent —$Y_2$—H or one $R_4'$=—$Y_2$—H and the other $R_4'$=chloro (—Cl), and more particularly both $R_4'$=—$Y_2$—H, with the proviso that in the case compound of formula $III^3$ in which both $R_4'$=chloro, the chloro group which did not form an amide with the amine compound of formula II is hydrolized in order to convert said chloro group to a hydroxy group (—OH), and converting compound of formula V to the compound of formula IX.

8. The process according to claim 7, wherein step (a) is carried out without isolation of an intermediate compound of formula IV

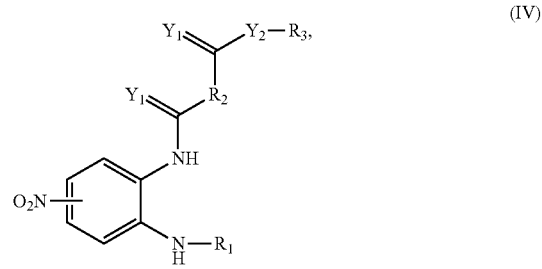

wherein $R_1$ represents alkyl, aryl or alkylaryl; $R_2$ represents alkanediyl, arylene, alkylarylene or arylalkanediyl; and $R_3$ represents H, alkyl, aryl or alkylaryl.

9. The process according to claim 7, wherein in the compound of formula V $R_1$ is C1-C3 alkyl, $R_2$ is C1-C3 alkanediyl, $R_3$ is H or C1-C3 alkyl; and particularly wherein in the compound of formula V, $R_1$ is $C_1$-$C_3$ alkyl, $R_2$ is $C_1$-$C_3$ alkanediyl, $R_3$ is H or $C_1$-$C_3$ alkyl; and/or in the compound of formula III$^1$, $R_4$=—$Y_2$—$CY_1$—$R_2$—$CY_1$—$Y_2$—$R_3'$.

10. A pharmaceutical composition comprising a compound of formula IX according to claim 1 in the form of a free acid/base or a pharmaceutically acceptable salt thereof as a pharmaceutically active agent(s) and at least one pharmaceutically acceptable excipient.

11. The pharmaceutical composition according to claim 10, wherein said composition is formulated for oral and/or parenteral administration.

12. A method of treating a disease, comprising administering an effective amount of the composition of claim 10 to a person in need thereof, wherein the disease is selected from the group consisting of acute T cell leukemia, erythroleukemia, Ewing osteosarcoma, (hormone dependent) mamma carcinoma, cervix carcinoma, colorectal cancer, medulloblastoma, glioblastoma and astrocytoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; and particularly selected from the group consisting of acute T cell leukaemia, erythroleukemia, Ewing osteosarcoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; and more particularly selected from the group consisting of Ewing osteosarcoma, malignant melanoma, pancreatic carcinoma, prostate cancer (metastasis of a subclavicular lymph node), colorectal adenocarcinoma, and osteosarcoma.

13. The compound according to claim 1, wherein $R_1$ is $C_1$-$C_4$ alkyl, and $R_2$ is $C_1$-$C_4$ alkanediyl.

14. The compound according to claim 1, wherein: $R_1$ is $C_1$-$C_3$ alkyl, and $R_2$ is $C_1$-$C_3$ alkanediyl.

15. The compound according to claim 1, wherein: $R_1$ is methyl, and $R_2$ is propanediyl.

\* \* \* \* \*